United States Patent
Lee et al.

(10) Patent No.: US 9,463,323 B2
(45) Date of Patent: Oct. 11, 2016

(54) SPATIALLY SELECTIVE NERVE STIMULATION IN HIGH-FREQUENCY NERVE CONDUCTION BLOCK AND RECRUITMENT

(75) Inventors: Dongchul Lee, Valencia, CA (US);
Bradley Hershey, Carrollton, TX (US);
Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1498 days.

(21) Appl. No.: 12/819,107

(22) Filed: Jun. 18, 2010

(65) Prior Publication Data
US 2010/0324630 A1    Dec. 23, 2010

Related U.S. Application Data

(60) Provisional application No. 61/218,297, filed on Jun. 18, 2009.

(51) Int. Cl.
*A61N 1/00* (2006.01)
*A61N 1/36* (2006.01)
*A61N 1/06* (2006.01)

(52) U.S. Cl.
CPC ............ *A61N 1/36167* (2013.01); *A61N 1/06* (2013.01); *A61N 1/36007* (2013.01); *A61N 1/36071* (2013.01)

(58) Field of Classification Search
CPC .............. A61N 1/06; A61N 1/36167; A61N 1/36071; A61N 1/36007
USPC .................................... 607/46, 117
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 6,928,320 B2 | 8/2005 | King | |
| 6,993,384 B2 | 1/2006 | Bradley et al. | |
| 7,539,538 B2 | 5/2009 | Parramon et al. | |
| 8,170,675 B2 * | 5/2012 | Alataris et al. | 607/46 |
| 2003/0139781 A1 | 7/2003 | Bradley et al. | |
| 2005/0267546 A1 | 12/2005 | Parramon et al. | |

* cited by examiner

*Primary Examiner* — Mallika D Fairchild
(74) *Attorney, Agent, or Firm* — Schwegman Lundberg & Woessner, P.A.

(57) ABSTRACT

A method of providing therapy to a patient using at least one electrode is provided. The patient has a neural tissue region that is relatively close to the at least one electrode, and a neural tissue region that is relatively far from the at least one electrode. The method comprises conveying time-varying electrical energy from the electrode(s) into the relatively close and far neural tissue regions, wherein the electrical energy has a frequency and amplitude that blocks stimulation of the relatively close neural tissue region, while stimulating the relatively far neural tissue region.

1 Claim, 6 Drawing Sheets

SPATIALLY SELECTIVE NERVE STIMULATION IN HIGH-FREQUENCY NERVE CONDUCTION BLOCK AND RECRUITMENT

RELATED APPLICATION

The present application claims the benefit under 35 U.S.C. §119 to U.S. provisional patent application Ser. No. 61/218,297, filed Jun. 18, 2009. The foregoing application is hereby incorporated by reference into the present application in its entirety.

FIELD OF THE INVENTION

The present inventions relate to tissue stimulation systems, and more particularly, to systems and methods for adjusting the stimulation provided to tissue to optimize a therapeutic effect.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, and rate of the stimulation pulses. The neurostimulation system may further comprise a handheld patient programmer to remotely instruct the neurostimulator to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

When stimulating neural tissue, the order in which nerve fibers are electrically stimulated or activated (i.e., the neural recruitment order), which is governed by spatial and morphometric criteria, has been a known issue that can limit efficacy by resulting in side effects (e.g., dorsal root stimulation, motor fiber stimulation, non-root-related effects, such as temperature, proprioceptor, reflex arc nerves, etc) that preclude the programming of stimulation systems to recruit fibers that could have possibly increased efficacy of the therapy.

For example, the neural recruitment order may be correlated to the diameter of the nerve fibers that innervate the volume of tissue to be stimulated. In SCS, activation (i.e., recruitment) of large diameter sensory fibers is believed to reduce/block transmission of smaller diameter pain fibers via interneuronal interaction in the dorsal horn of the spinal cord. Activation of large sensory fibers also creates a sensation known as paresthesia that can be characterized as an alternative sensation that replaces the pain signals sensed by the patient.

Because larger nerve fibers have lower stimulation thresholds than smaller nerve fibers, the larger nerve fibers will normally be stimulated before smaller nerve fibers when located the same distance from the active electrode or electrodes. Because of this, over-stimulation of nerve fibers closest to the active electrode(s) is often unavoidable, thereby leading to uncomfortable, intense sensations in unwanted areas, and in the case of SCS, preventing the recruitment of deeper and/or smaller nerve fibers that might increase the efficacy of the therapy.

Thus, a neurostimulation system that could modify the recruitment order with respect to depth of nerve fibers, such that deeper nerve fibers are recruited more preferentially than shallower nerve fibers, would be valuable to "tune" the desired therapeutic effect of a neurostimulation application, such as SCS.

SUMMARY OF THE INVENTION

In accordance with the present inventions, a method of providing therapy to a patient using at least one electrode is provided. The patient has a neural tissue region that is relatively close to the electrode(s), and a neural tissue region that is relatively far from the electrode(s). The relatively close neural tissue region results in a side-effect when stimulated to a particular degree, and the relatively far neural tissue region results in therapy when stimulated. The method comprises conveying time-varying electrical energy (e.g., sinusoidal) from the electrode(s) into the relatively close and far neural tissue regions. The electrical energy has a frequency and amplitude that blocks stimulation of the relatively close neural tissue region, while stimulating the relatively far neural tissue region. In one method, the time-varying electrical energy is generated using a hybrid of multiple frequencies. In another method, the relatively close neural tissue region and the relative far neural tissue region are located in the spinal cord of the patient. In this case, the relatively close neural tissue region may comprise superficial dorsal column nerve fibers, and the relatively far neural tissue region comprises non-superficial dorsal column nerve fibers.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
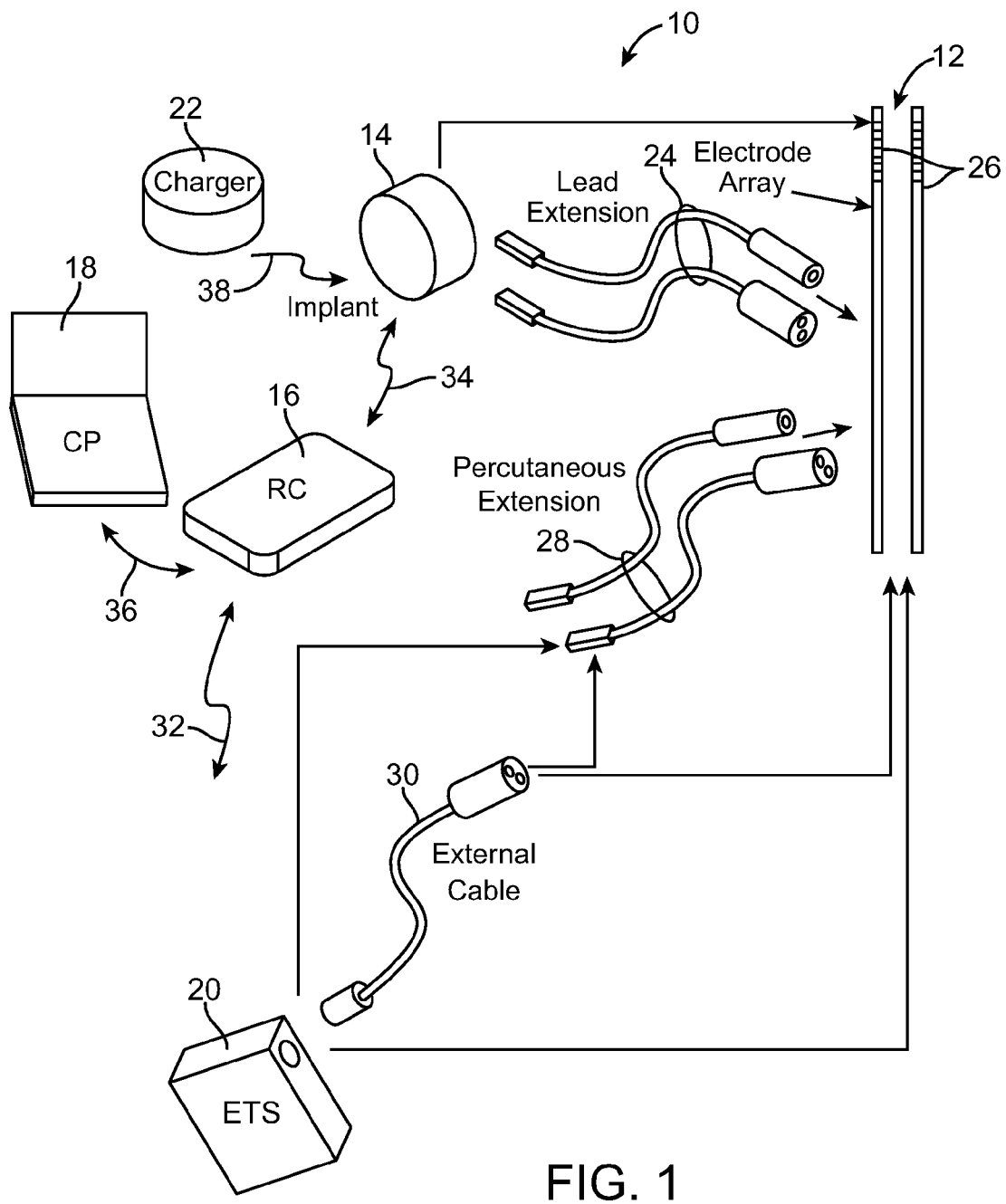
FIG. 1 is plan view of one embodiment of a spinal cord stimulation (SCS) system arranged in accordance with the present inventions.

Turning first to FIG. 1, an exemplary SCS system 10 generally includes one or more (in this case, two) implantable stimulation leads 12, an implantable neurostimulator 14, an external remote controller RC 16, a clinician's programmer (CP) 18, an External Trial Stimulator (ETS) 20, and an external charger 22.

The neurostimulator 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the neurostimulator 14 includes pulse generation circuitry that delivers the electrical stimulation energy in the form of a time-varying waveform in accordance with a set of stimulation parameters.

The ETS 20 may also be physically connected via the percutaneous lead extensions 28 and external cable 30 to the stimulation leads 12. The ETS 20, which has similar pulse generation circuitry as the neurostimulator 14, also delivers electrical stimulation energy to the electrode array 26 accordance with a set of stimulation parameters. The major difference between the ETS 20 and the neurostimulator 14 is that the ETS 20 is a non-implantable device that is used on a trial basis after the stimulation leads 12 have been implanted and prior to implantation of the neurostimulator 14, to test the responsiveness of the stimulation that is to be provided.

The RC 16 may be used to telemetrically control the ETS 20 via a bi-directional RF communications link 32. Once the neurostimulator 14 and stimulation leads 12 are implanted, the RC 16 may be used to telemetrically control the neurostimulator 14 via a bi-directional RF communications link 34. Such control allows the neurostimulator 14 to be turned on or off and to be programmed with different stimulation parameter sets. The neurostimulator 14 may also be operated to modify the programmed stimulation parameters to actively control the characteristics of the electrical stimulation energy output by the neurostimulator 14. The CP 18 provides clinician detailed stimulation parameters for programming the neurostimulator 14 and ETS 20 in the operating room and in follow-up sessions. The CP 18 may perform this function by indirectly communicating with the neurostimulator 14 or ETS 20, through the RC 16, via an IR communications link 36. Alternatively, the CP 18 may directly communicate with the neurostimulator 14 or ETS 20 via an RF communications link (not shown). The external charger 22 is a portable device used to transcutaneously charge the neurostimulator 14 via an inductive link 38. Once the neurostimulator 14 has been programmed, and its power source has been charged by the external charger 22 or otherwise replenished, the neurostimulator 14 may function as programmed without the RC 16 or CP 18 being present.

For purposes of brevity, the details of the RC 16, CPS 18, ETS 20, and external charger 22 will not be described herein. Details of exemplary embodiments of these devices are disclosed in U.S. Pat. No. 6,895,280, which is expressly incorporated herein by reference.

Figure 2:
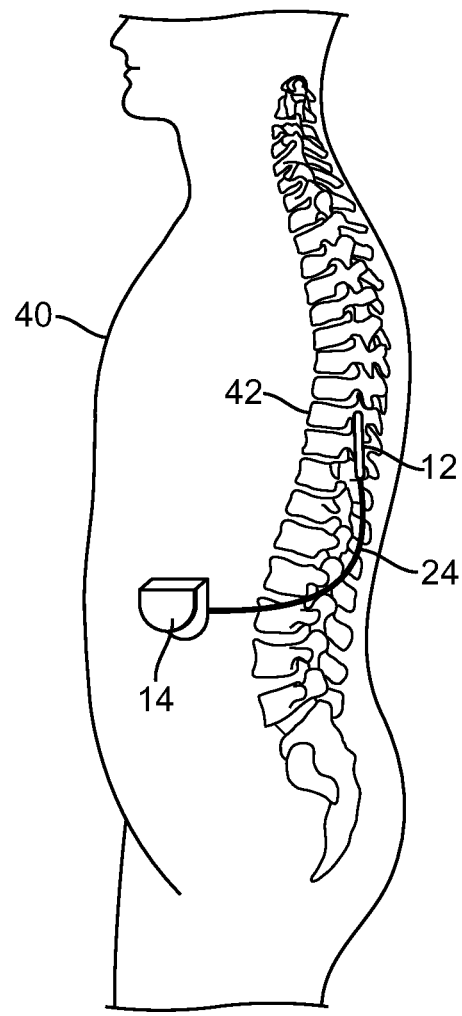
FIG. 2 is a plan view of the SCS system of FIG. 1 in use with a patient.

As shown in FIG. 2, the electrode lead 12 is implanted within the spinal column 42 of a patient 40. The preferred placement of the electrode lead 12 is adjacent, i.e., resting upon, the spinal cord area to be stimulated. Due to the lack of space near the location where the electrode leads 12 exit the spinal column 42, the neurostimulator 14 is generally implanted in a surgically-made pocket either in the abdomen or above the buttocks. The neurostimulator 14 may, of course, also be implanted in other locations of the patient's body. The lead extension 24 facilitates locating the neurostimulator 14 away from the exit point of the electrode leads 12. As there shown, the CP 18 communicates with the neurostimulator 14 via the RC 16.

Figure 3:
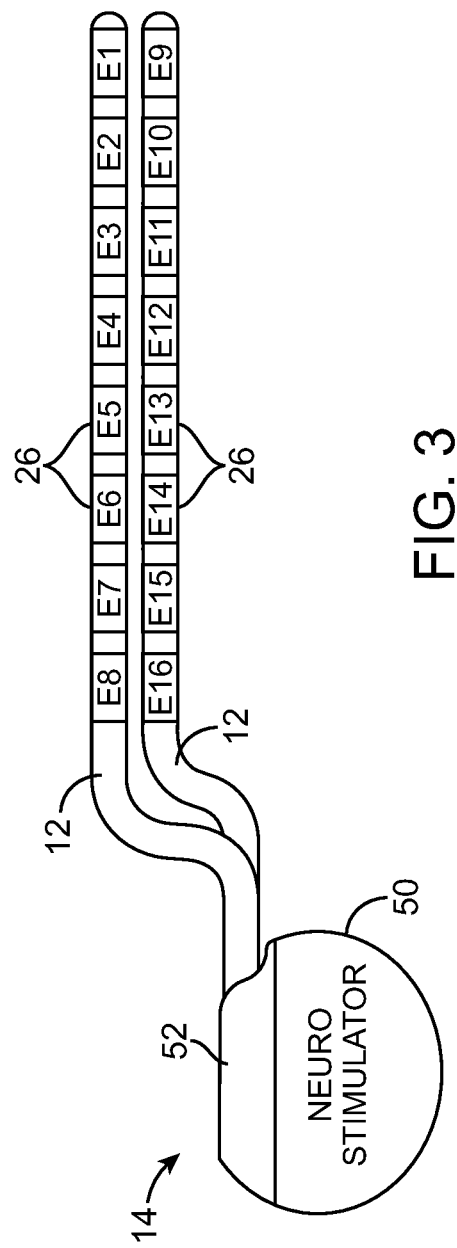
FIG. 3 is a plan view of an implantable pulse generator (IPG) and one embodiment of a stimulation lead used in the SCS system of FIG. 1.

Referring now to FIG. 3, the external features of the stimulation leads 12 and the neurostimulator 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The neurostimulator 14 comprises an outer case 50 for housing the electronic and other components (described in further detail below), and a connector 52 to which the proximal ends of the stimulation leads 12 mate in a manner that electrically couples the electrodes 26 to the internal electronics (described in further detail below) within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

As briefly discussed above, the neurostimulator 14 includes circuitry that delivers the electrical stimulation energy to the electrode array 26 in accordance with a set of stimulation parameters programmed into the neurostimulator 14. Such stimulation parameters may comprise electrode combinations, which define the electrodes that are activated and turned off (zero), percentage of stimulation energy assigned to each electrode (fractionalized electrode configurations), and electrical parameters, which define the pulse amplitude (measured in milliamps or volts depending on whether the neurostimulator 14 supplies constant current or constant voltage to the electrode array 26), and frequency (measured in Hertz).

Figure 4:
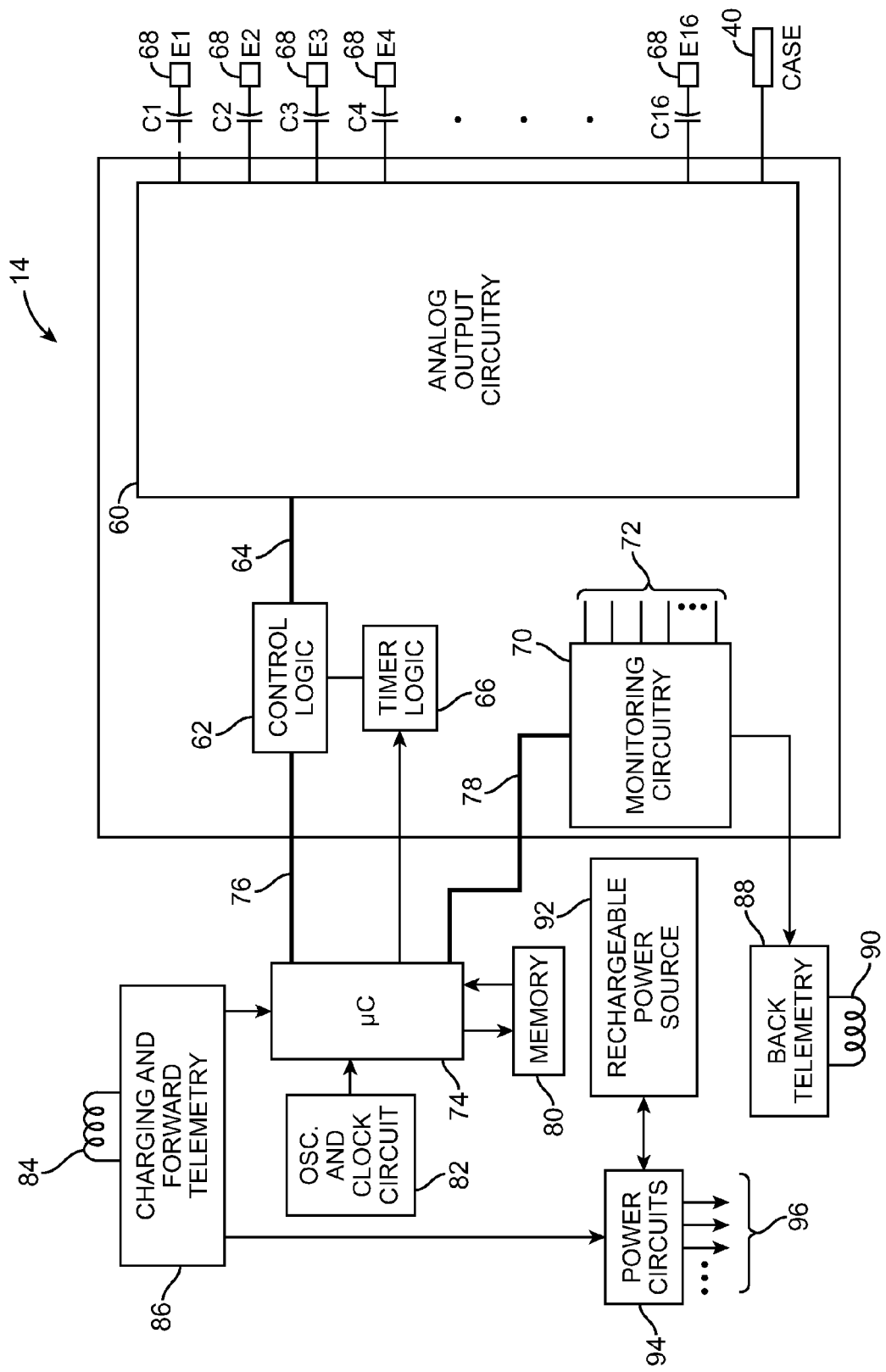
FIG. 4 is a block diagram of the internal components of the IPG of FIG. 3.

Turning next to FIG. 4, the main internal components of the neurostimulator 14 will now be described. The neurostimulator 14 includes stimulation output circuitry 60 configured for generating electrical stimulation energy in accordance with a defined waveform having a specified amplitude and frequency control of control logic 62 over data bus 64. Control of the frequency of the electrical waveform is facilitated by timer logic circuitry 66, which may have a suitable resolution, e.g., 10 µs. The stimulation energy generated by the analog output circuitry 60 is output via capacitors C1-C16 to electrical terminals 68 corresponding to the electrodes 26.

In the preferred embodiment, the analog output circuitry 60 comprises independently controlled current sources for providing stimulation pulses of a specified and known amperage to or from the electrical terminals 68, although in alternative embodiments, the analog output circuitry 60 may comprise independently controlled voltage sources for providing stimulation pulses of a specified and known voltage at the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The neurostimulator 14 further comprises monitoring circuitry 70 for monitoring the status of various nodes or other points 72 throughout the neurostimulator 14, e.g., power supply voltages, temperature, battery voltage, and the like. The monitoring circuitry 70 is also configured for measuring electrical parameter data (e.g., electrode impedance and/or electrode field potential). The neurostimulator 14 further comprises processing circuitry in the form of a microcontroller (µC) 74 that controls the control logic 62 over data bus 76, and obtains status data from the monitoring circuitry 70 via data bus 78. The neurostimulator 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the neurostimulator 14 in accordance with a selected operating program and stimulation parameters. In controlling the operation of the neurostimulator 14, the microcontroller 74 is able to individually generate stimulation energy at the electrical terminals 68 using the analog output circuitry 60, in combination with the control logic 62 and timer logic circuitry 66. The microcontroller 74 facilitates the storage of electrical parameter data measured by the monitoring circuitry 70 within memory 80.

The neurostimulator 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the neurostimulator 14.

The neurostimulator 14 further comprises back telemetry circuitry 88 and a transmission coil 90 for sending informational data to the external programmer. The back telemetry features of the neurostimulator 14 also allow its status to be checked. For example, when the CP 18 initiates a programming session with the neurostimulator 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the neurostimulator 14 may be uploaded to the CP 18.

The neurostimulator 14 further comprises a rechargeable power source 92 and power circuits 94 for providing the operating power to the neurostimulator 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the neurostimulator 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 1), which generates the AC magnetic field, is placed against, or otherwise adjacent, to the patient's skin over the implanted neurostimulator 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Significant to the present inventions, the neurostimulator 14 may be operated in a manner that blocks the stimulation of nerve fibers relatively close to the active electrode(s) and stimulates nerve fibers that are relatively far from the active electrode(s). In particular, the neurostimulation 14 generates and conveys high frequency electrical energy from the active electrode(s) to the relatively close and far nerve fibers. A conventional neural fiber modeling technique shows that high frequency electrical energy (greater than 2.2 kHz) blocks stimulation of a nerve fiber at a certain threshold.

Figure 5:
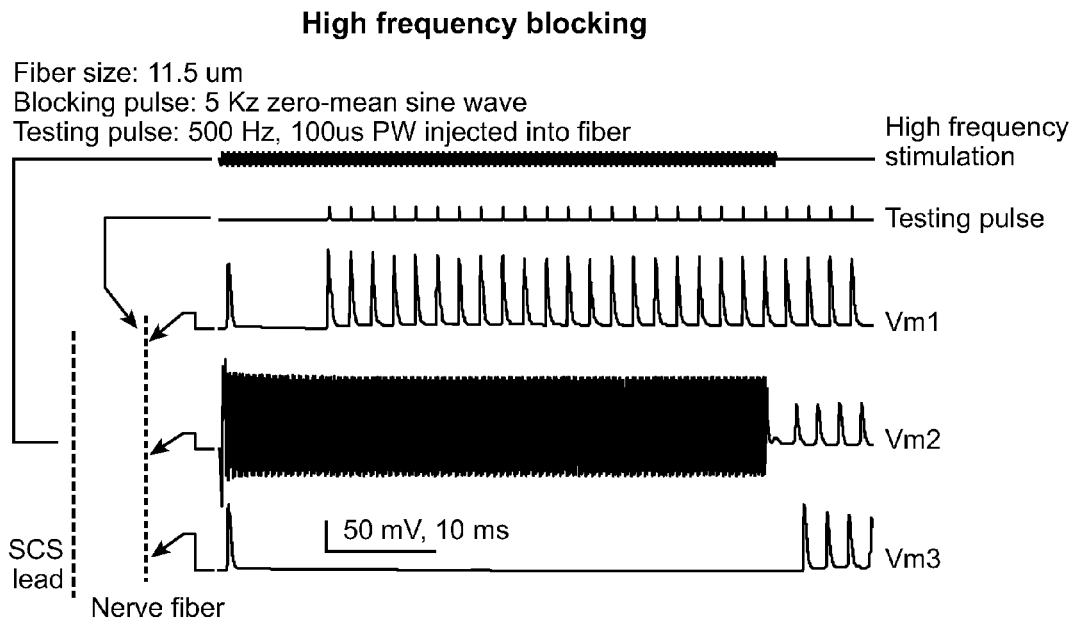
FIG. 5 is a diagram illustrating the blocking of a nerve fiber using high frequency electrical energy.

For example, with reference to FIG. 5, high frequency electrical energy having a zero-mean 5 KHz sinusoidal waveform was applied from an electrode to a modeled 11.5 µm diameter nerve fiber. During the application of the high frequency electrical energy, a test pulse train was applied to the end of the modeled nerve fiber. As shown, action potentials (measured as the membrane voltage $Vm1$) generated by the test pulse train were blocked at nodes close to the high frequency electrode (measured as the membrane voltage $Vm2$), and therefore, could not propagate toward the other end of the nerve fiber (measured as the membrane voltage $Vm3$).

Significantly, the blocking threshold of a nerve fiber by high frequency electrical energy is higher than the threshold at which the nerve fiber is activated by the same high frequency electrical energy. Thus, if the high frequency electrical energy has an amplitude that is higher than the blocking threshold of superficial dorsal column nerve fibers, the non-superficial dorsal nerve fibers at a particular depth will still have a blocking threshold above the amplitude of the high frequency electrical energy, but a stimulation threshold below the amplitude of the high frequency electrical energy. This means that superficial dorsal column nerve fibers will be blocked at a stimulation current that activates non-superficial dorsal column fibers.

Figure 6:
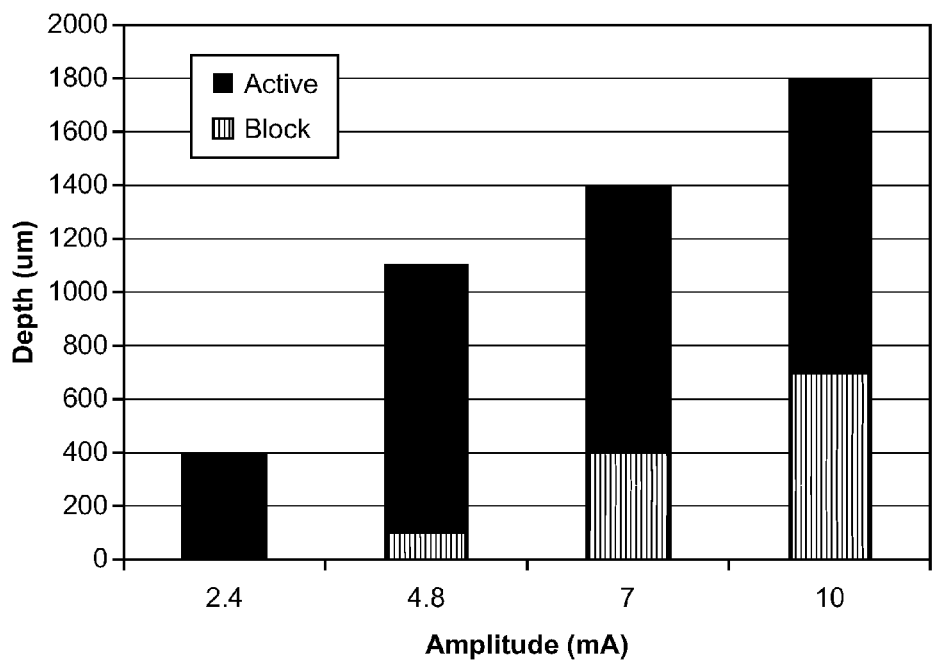
FIG. 6 is a bar graph illustrating the blocking depths and activation depths of nerve fibers plotted against the amplitude of high frequency electrical energy generated by a neurostimulator used in the system of FIG. 1.

For example, with reference to FIG. 6, nerve fiber blocking and stimulation as a function of high frequency electrical energy amplitude was modeled for 11.5 µm diameter nerve fibers on the midline of a spinal cord dorsal column area. As shown, for a relatively low amplitude (2.4 mA), nerve fibers up to 400 µm deep into the dorsal column were all stimulated. As the amplitude of the high frequency electrical energy was increased (4.8 mA), the blocking threshold of the superficial nerve fibers was exceeded, such that nerve fibers up to a depth of 100 µm were blocked, while the depth of the stimulated nerve fibers was increased to a range of 100-1100 µm. As the amplitude of the high frequency electrical energy was further increased (7.0 mA), the depth of the blocked nerve fibers was increased to 400 µm, while the depth of the activated nerve fibers was increased to a range of 400-1400 µm. Further increasing the amplitude of the high frequency electrical energy (10 mA) further increased the depth of the blocked nerve fibers to 700 µm and further increased the depth of the stimulation nerve fibers to a range of 700-1800 µm. Thus, it can be appreciated the desired depth range of blocked nerve fibers and the desired depth range of the stimulation nerve fibers may be tuned by selecting the amplitude of the high frequency electrical energy.

Figure 7:
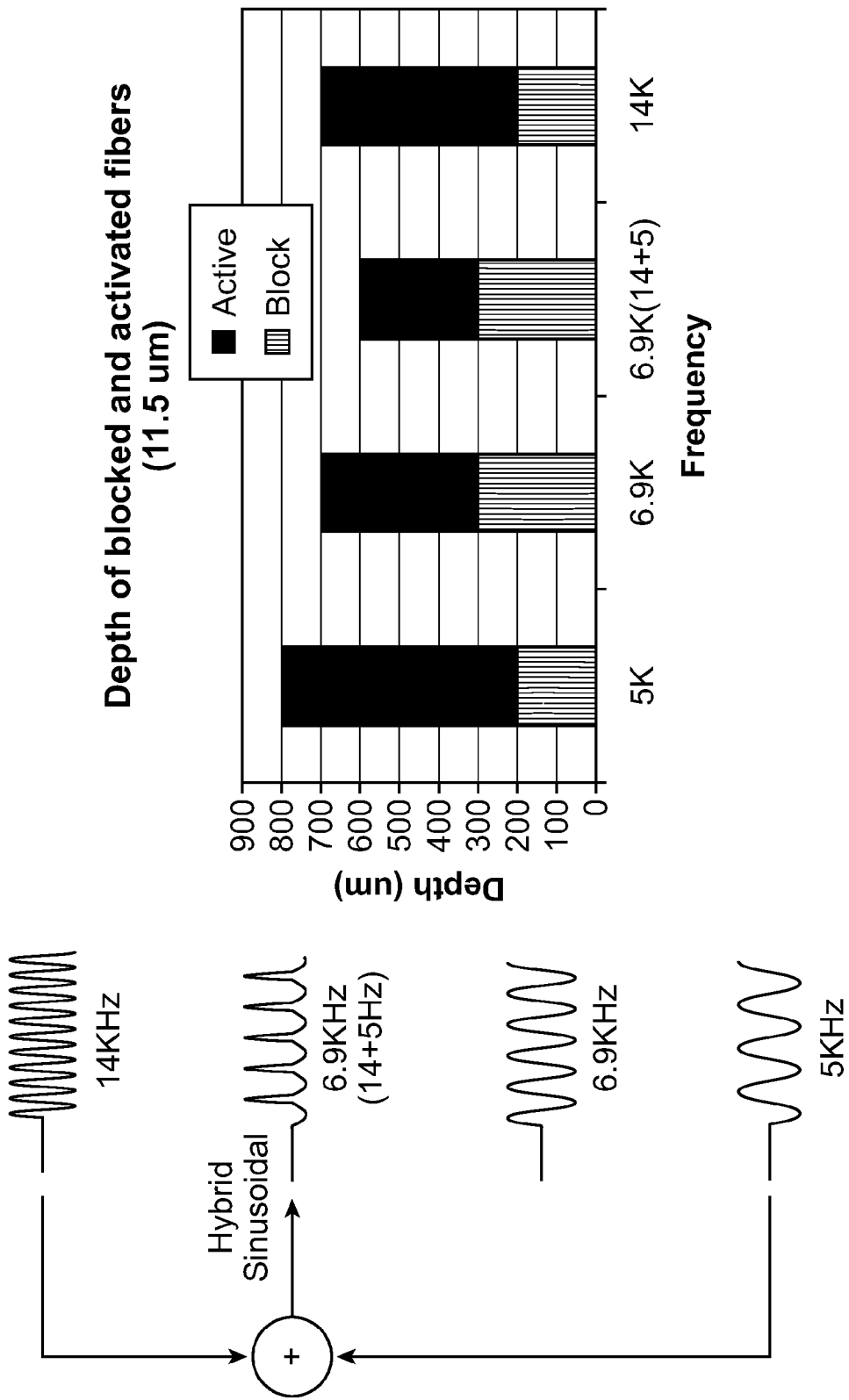
FIG. 7 is a bar graph illustrating the blocking depths and activation depths of nerve fibers plotted against the frequency of high frequency electrical energy generated by a neurostimulator used in the system of FIG. 1.

The desired depth range of blocked nerve fibers and the desired depth range of the stimulation nerve fibers may be tuned by also selecting the frequency of the electrical energy. For example, as shown in FIG. 7, using a 2.4 mA amplitude for the high frequency stimulation energy, the depth of the blocked nerve fibers was up to 200 µm, and the depth of the stimulated nerve fibers was in the range of 200 µm-800 µm for a frequency of 5 KHz. The depth of the blocked nerve fibers was up to 300 µm, and the depth of the stimulated nerve fibers was in the range of 300 µm-700 µm for a frequency of 6.9 KHz. The depth of the blocked nerve fibers was up to 200 µm, and the depth of the stimulated nerve fibers was in the range of 200 µm-700 µm for a frequency of 14 KHz.

The desired depth range of blocked nerve fibers and the desired depth range of the stimulation nerve fibers may also be tuned by using hybrid sinusoidal waveforms that have been created by combining sinusoidal waveforms of two different frequencies. For example, as shown in FIG. 7, a 6.9 kHz hybrid sinusoidal waveform was created by combining half phases of 5 kHz and 14 kHz. As illustrated, the depth ranges of the respective blocked nerve fibers and the stimulation nerve fibers resulting from the 6.9 kHz hybrid sinusoidal waveform are different from the depth ranges of the respective blocked nerve fibers and the stimulation nerve fibers resulting from the pure 5 kHz, 6.9 kHz, and 14 kHz sinusoidal waveforms. Notably, the ratio between the blocked and stimulated nerve fiber depth is lowest using the hybrid sinusoidal waveform. Notably, if it is desired to minimize the activated region (which implies greater nerve selectivity), a hybrid sinusoidal waveform (6.9K) is preferred, because it blocks nerve fibers as deep as would a typical 6.9 kHz sinusoidal waveform, but activates nerve fibers less deep than would a typical 6.9 kHz sinusoidal waveform. The neurostimulator 14 may generate the hybrid sinusoidal waveform in response to an input from the user (e.g., via the RC 16 or CP 18) of the two frequencies that are to be mixed to generate the hybrid sinusoidal waveform.

Thus, it can be appreciated that by controlling the depth at which nerve fibers are both blocked and stimulated, the dorsal column nerve fibers relatively close to the activate electrode(s), which presumably will create an adverse side-effect if stimulated, can be blocked, whereas the dorsal column nerve fibers relatively far from the active electrode(s), which presumably will provide the necessary therapy if stimulated, can be activated.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient using at least one electrode, the patient having a neural tissue region that is relatively close to the at least one electrode, and a neural tissue region that is relatively far from the at least one electrode, the method comprising:
   conveying time-varying electrical energy from the at least one electrode into the relatively close and far neural tissue regions, wherein the electrical energy has a frequency and amplitude that blocks stimulation of the relatively close neural tissue region, while stimulating the relatively far neural tissue region,
   wherein the relatively close neural tissue region results in a side-effect when stimulated, and the relatively far neural tissue region results in therapy when stimulated.

* * * * *